United States Patent
Giesel et al.

(10) Patent No.: US 8,369,925 B2
(45) Date of Patent: Feb. 5, 2013

(54) METHOD TO DERIVE ANATOMICAL AND/OR PATHOLOGICAL STRUCTURES FROM DATA OF IMAGING TECHNOLOGIES

(75) Inventors: Frederik Giesel, Heidelberg (DE); Christian Zechmann, Eppelheim (DE); Hendrik Von Tengg-Kobligk, Dossenheim (DE); Marc Muenter, Heidelberg (DE); Juergen Debus, Heidelberg (DE); Rainer Neumann, Gross-Gerau (DE); Ulrike Ute Neumann née Pitsch, legal representative, Groβ-Gerau (DE)

(73) Assignees: DKFZ Deutsches Krebsforschungszentrum Stiftung des oeffentlichen Rechts, Heidelberg (DE); Ruprecht-Karls-Universitaet Heidelberg, Heidelberg (DE)

( * ) Notice: Subject to any disclaimer, the term of this patent is extended or adjusted under 35 U.S.C. 154(b) by 104 days.

(21) Appl. No.: 12/903,821

(22) Filed: Oct. 13, 2010

(65) Prior Publication Data

US 2011/0118527 A1    May 19, 2011

Related U.S. Application Data

(63) Continuation of application No. PCT/EP2009/002717, filed on Apr. 14, 2009.

(60) Provisional application No. 61/044,600, filed on Apr. 14, 2008.

(30) Foreign Application Priority Data

Apr. 14, 2008  (EP) .................................. 08154476

(51) Int. Cl.
*A61B 5/05*   (2006.01)

(52) U.S. Cl. ......................... 600/407; 600/410; 606/130
(58) Field of Classification Search ................. 600/407, 600/410, 411, 427, 429; 606/130
See application file for complete search history.

(56) References Cited

U.S. PATENT DOCUMENTS 6,310,355 B1  10/2001  Cadwalader
(Continued)

FOREIGN PATENT DOCUMENTS

| EP | 1 277 768 B1 | 8/2002 |
|---|---|---|
| WO | WO 01/64106 A1 | 9/2001 |

(Continued)

OTHER PUBLICATIONS

Deformable and rigid registration of MRI and microPET images for photodynamic therapy of cancer in mice, pp. 753-760 in Medical Physics., AIP, Melville, NY, US, vol. 33, 3, Feb. 23, 2006; ISSN 0094-2405.

(Continued)

*Primary Examiner* — James Kish
*Assistant Examiner* — Michael N Fisher
(74) *Attorney, Agent, or Firm* — Muncy, Geissler, Olds & Lowe, PLLC

(57) ABSTRACT

A method to derive anatomical structures from non-invasive imaging technologies is provided. Non-invasive imaging technologies are computed tomography (CT), magnetic resonance imaging (MRI), positron emission tomography (PET), surface scans and others. Imaging data obtained by a non-invasive technology is used to create a surface contour. The imaging data is transmitted to a rapid prototyping apparatus as readable data. With this readable data the rapid prototyping apparatus establishes a positive or negative surface model, such as a fixation device, a mask, or a prosthesis, or other instruments for medical purposes.

27 Claims, 7 Drawing Sheets

U.S. PATENT DOCUMENTS

| | | | |
|---|---|---|---|
| 6,430,430 B1* | 8/2002 | Gosche | 600/410 |
| 6,459,927 B1 | 10/2002 | Franklin et al. | |
| 7,024,237 B1* | 4/2006 | Bova et al. | 600/429 |
| 2002/0062909 A1* | 5/2002 | Jang et al. | 156/155 |
| 2003/0023156 A1* | 1/2003 | Pappas et al. | 600/407 |
| 2004/0036838 A1* | 2/2004 | Podoleanu et al. | 351/206 |
| 2005/0075649 A1* | 4/2005 | Bova et al. | 606/130 |
| 2005/0080332 A1* | 4/2005 | Shiu et al. | 600/411 |
| 2006/0094951 A1* | 5/2006 | Dean et al. | 600/407 |

FOREIGN PATENT DOCUMENTS

WO    WO 2004/110309 A2    12/2004

OTHER PUBLICATIONS

Gehl, G. Sailer, H.F. Zollikofer, C.E. Stucki, P.: Epithetic Treatment Principles and Use of Stereolithography, Journal of Cranio-Maxillofacial Surgery. vol. 24, Supplement 1, 1996, 46.

* cited by examiner

Fig. 1.1

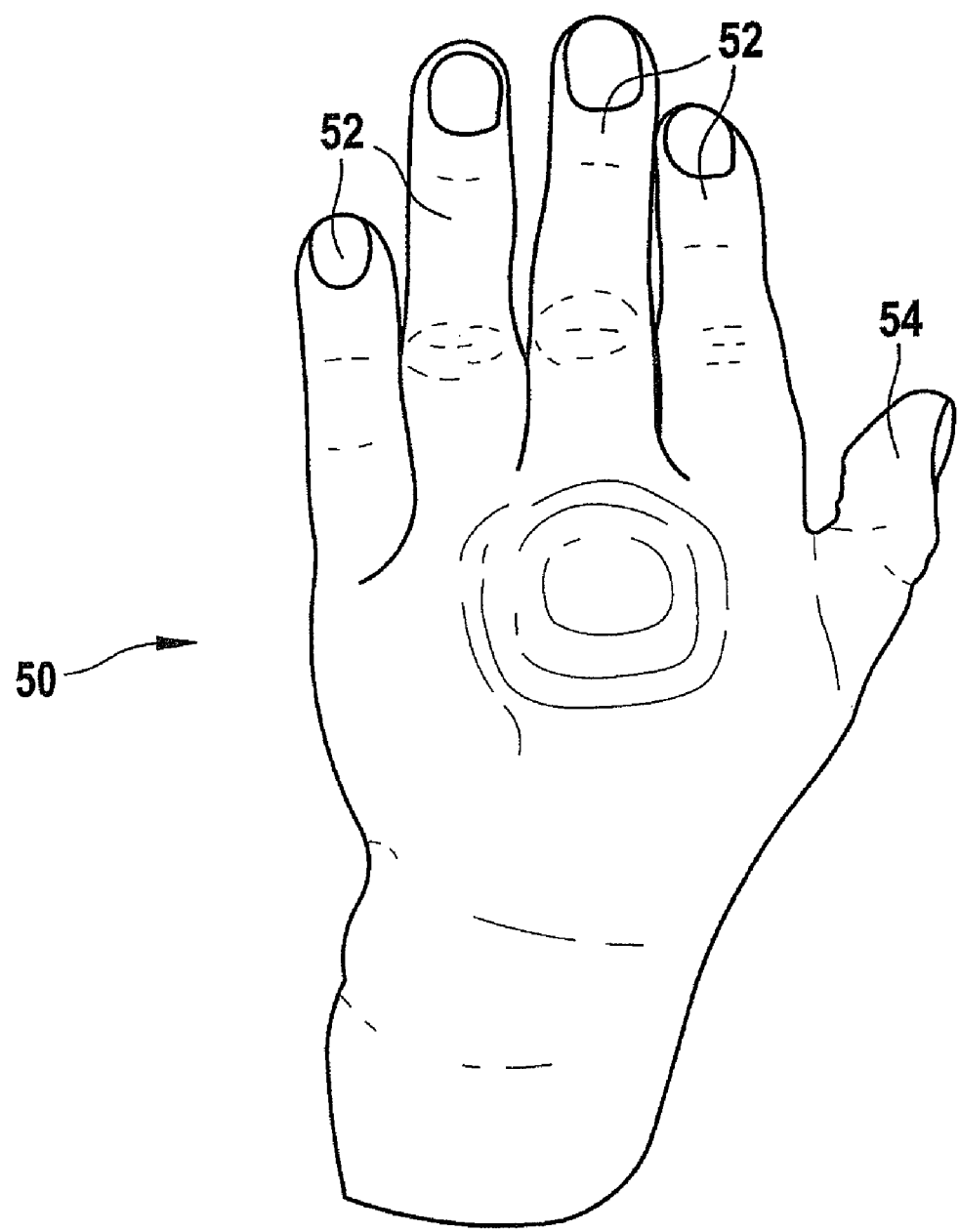
Fig. 5.1

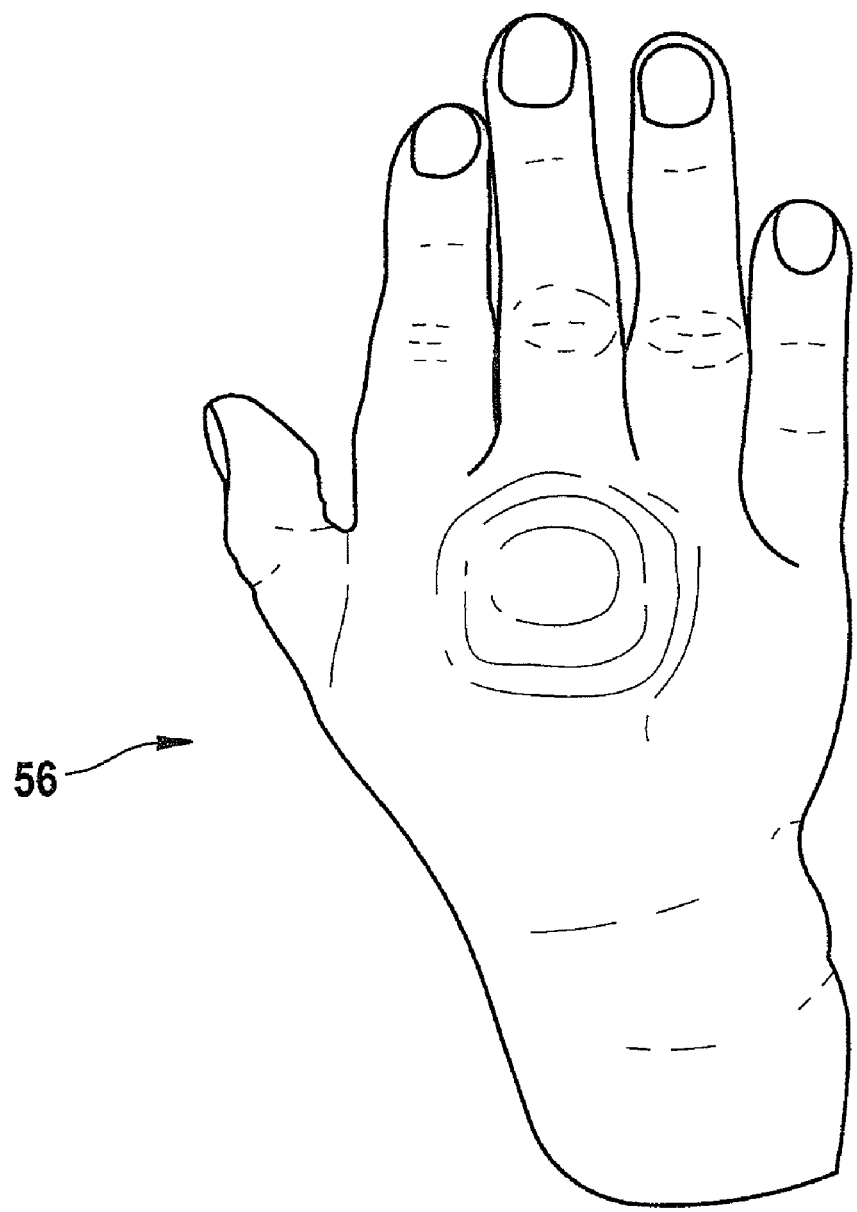
Fig. 5.2

METHOD TO DERIVE ANATOMICAL AND/OR PATHOLOGICAL STRUCTURES FROM DATA OF IMAGING TECHNOLOGIES

This nonprovisional application is a continuation of International Application No. PCT/EP2009/002717, which was filed on Apr. 14, 2009, and which claims priority to European Patent Application No. 08154476.9, which was filed on Apr. 14, 2008, and which claims priority to U.S. Provisional Application No. 61/044,600, which was filed on Apr. 14, 2008 and which are all herein incorporated by reference.

BACKGROUND OF THE INVENTION

1. Field of the Invention

The present invention relates to a method to derive anatomical and/or pathological structures using digital imaging data by non-invasive imaging technologies such as computer tomography (CT) or magnetic resonance imaging (MRI) as well as optical, ultrasound or laser-based scanners. These techniques involve different key areas: To start with, one key area is the reproduction of individual body surfaces (forms) for radiotherapy treatment planning, follow-up and functional imaging. A further key area is the reprint of an anatomical structure or an organ of the human body for preoperative planning, surgery support and guidance, teaching tools for validation of bioengineering computed simulation and prosthesis generation or manufacturing, respectively.

2. Description of the Background Art

The problem at the moment is a manual production and adaption of masks for radiotherapeutic treatment planning. Theses processes are quite time consuming and not very accurate in fitting to the individual patient's body geometry.

In radiation therapy, tumorous tissue is treated with high-energy beams. The application has to be exactly controlled in order to deliver the dose to the entire tumor and to minimize damage to neighboring healthy tissue. Since most of the radiation therapy is performed by an external radiation therapy device such as a linear accelerator which produces high energy X-rays, healthy tissue usually is affected by radiation as well. Therefore, planning procedures are used to calculate the dosage to be delivered to the tumor and describe as well its dosage to normal tissue. In order to minimize irradiation of healthy tissue and to maximize the amount of dose delivered to the tumor, several angulated radiation beams converging to the tumor site are used. To achieve this, an exact reproducible and stable positioning of the body part affected is of utmost importance.

Also the performance of a stereotactic procedure or an operation requires exact fixation and positioning of the relevant body part in order to localize and target the region of interest.

One method of fixating a body part is to attach fixation rings, e.g. to the skull, which require the attachment of sharpened screws to the bone of the patient. EP 1 227 768 B1 gives an example for a method of designing customizable fixture for patient positioning. According to this disclosure, a method of designing a customized positioning fixture for positioning a body in relation to a medical apparatus comprises the following steps:

First, determination of body mounting data from a scanned image characterizing positions of a plurality of mounting devices on the body is accomplished. This mounting data is used to compute a digital model of the positioning fixture that characterizes a shape of the positioning fixture such that the shape includes a first plurality of mounting structures for meeting with the mounting device on the body and a second plurality of mounting structures for attaching the positioning fixture to the medical apparatus to hold the body in a predetermined position relative to the medical apparatus.

Another frequently used procedure is to plaster a cast around a body part with plastic material. However, this method comes along with several disadvantages. One of them worth mentioning is the duration of winding the plastic cast and a hardening time of about 20 minutes. During this period of time, the patient cannot move, the plaster is warming up and the plaster cannot be removed very quickly. Also an opening of the mask is quite uncomfortable for the patient since the plaster has to be cut open after the mask has adopted a sufficient stability while it is still attached to the patient. Therefore, this method is extremely unpleasant for patients with claustrophobia or young children. At present, sparing out foramina for e.g. eyes, ears or the nose is not possible during the production of the masks.

U.S. Pat. No. 6,459,927 is related to a method for positioning a body in relation to a medical apparatus using a customized positioning fixture comprising: providing a 3-D scanned image of the body; determining from the scanned image of the body mounting data that characterizes positions of a plurality of mounting location on the body; using the mounting data computing a digital model of the positioning fixture such that the shape includes a first plurality of mounting structures that mate with the mounting locations on the body, and a second plurality of mounting structures for attaching the positioning fixture to the medical apparatus; fabricating the positioning fixture according to the digital model; fixing the body to the medical apparatus in a predetermined position of the body relative to the medical apparatus, including mating different plurality of mounting structures with the mounting locations on the body and attaching the positioning fixture to the medical apparatus using the second plurality of mounting structures.

US 2005/0075649 A1 is related to a frameless stereo active guidance of image-based medical procedures. A device for guiding medical procedures is disclosed, which comprises at least subject-specific article comprising at least one reference contour dimensioned to follow a contour of an exterior surface portion of a subject to be treated. The at least one subject-specific article is rigidly attachable to the surface portion, wherein the subject-specific articles provides a customized spatial reference for alignment of a preplanned medical procedure to one or more target regions of the subject. The at least one subject-specific article is to be placed on the subject and a medical procedure is performed on the target region, guided at least in part by the subject-specific article.

WO 2004/110309 A2 is related to a computer-aided design of skeletal implants. A computer-aided design method for producing an implant for a patient prior to operation comprises the steps of generating data with a non-invasive 3-D (3-dimensional) scan of the patient's defect site that digitally represents the area that will receive the implant. Designing and validating an implant on a computer based on digital data generated from a volume image of the patient is performed. Still further, the implant is fabricated based solely on the implant design data generated on computer. Still further, the step of designing an implant based on the data generated from the 3-D scan of a patient is including the step of constructing a surface image representing a patient's defect site from 3-D volume images. The step of generating data includes defining a contour, describing the external boundary of the patient's defect site to receive the implant on the surface image representing a patient's defect site that is derived from the 3-D volume images in an accurate 3-D space.

U.S. Pat. No. 6,310,355 B1 is related to a lightweight radiation shield system. A shield is disclosed for attenuating the flux of electromagnetic radiation from an article. The shield comprises a flexible matrix comprising a film including a radiation attenuating material, the matrix including at least one space within the matrix. The at least one space reduces the weight of the shield without appreciably reducing the attenuating characteristics of the shield.

WO 01/64106 A1 is related to animation technology. A method is disclosed for producing 3-dimensional visualizations of digital representations of cross-sectional slices of a vertebrate animal or human body part and includes the following steps: A first ordered series of slices of a portion of the body part in a first position is obtained. One or more filters are applied to each of the digital representations of the first ordered series of slices to identify the skeletal portions of the body part. The first filtered series is converted into a 3-dimensional representation of the skeleton of the body part in the first position. A second ordered series of slices of the portion of the body part in a second position different to the first position is obtained. One or more filters are applied to each of the digital representations of the second ordered series of slices to identify the skeletal portions of the body part. The second filtered series is converted into 3-dimensional representation of the skeleton of the body part in the second position and the 3-dimensional representations are combined to form a step frame animation having as many steps as there are ordered series of slices.

The publication "Deformable and rigid registration of MRI and microPET images for photodynamic therapy of cancer in mice", pages 753-760 in Medical Physics, AIP, Melville, N.Y., US, vol. 33, 3, 23 Feb. 2006, ISSN: 0094-2405 discloses an investigation of imaging techniques to study the tumor response to photodynamic therapy. Positron emission tomography provides physiological and functional information. High-resolution magnetic resonance imaging provides anatomical and morphological changes. Image registration can combine MRI and PET images for improved tumor monitoring. In high resolution MRI and microPET F-flourodeoxyglucose images from C3H mice with RIF-1 tumors were treated with Pc 4-based photodynamic therapy. For registration of the whole mouse body, an automatic three-dimensional, normalized mutual information algorithm is used. For registration of tumor a whole body registration has been developed performing slice-by-slice review of both image volumes. Manually segmented feature organs such as the left and right kidneys and the bladder are present in each slice, being computed and the distance between corresponding centroids has been computed. The distance between corresponding centroids of organs was found to be 1.5+−0.4 mm, corresponding to about 2 pixels of microPET images. The mean volume overlap ratios for tumors were 94.7% and 86.3% for the deformable and rigid registration methods, respectively.

SUMMARY OF THE INVENTION

An object of the present invention is to avoid disadvantageous techniques such as attaching fixation rings to the skull requiring the attachment of sharpened screws to the bone of the patient as well as to avoid plaster casting of the body part with plastic material coming along with the disadvantages outlined above.

A further object of the present invention is to cut costs in radiation therapy and individual radiation therapy by providing a standardized method (rapid prototyping) to produce individual masks required for radiation therapy treatment.

A further object of the present invention is to use more efficiently data obtained from non-invasive imaging technologies such as computed tomography (CT) and magnetic resonance imaging (MRI), as well as 3-D optical imaging, ultrasound or laser scanners (3DS).

According to one aspect of the present invention, a fixation device for treatment planning, radiation therapy equipment or stereotactic application is disclosed. The fixation device according to the present invention is used in conjunction with a patient positioning couch on either an imaging device such as CT, MRI or positron emission tomography (PET) or others. The fixation device, particularly a mask, obtained from previously applied non-invasive imaging technologies, such as CT, MRI, 3-D optical imaging, ultrasound or laser scanners, have advantages over current solutions, obtained by plaster casting involving the drawbacks outlined above.

Imaging data acquired by non-invasive imaging is post-processed into a surface model with or without off-set to the skin surface. Data is then transferred to a dedicated work station with special image post-processing software. Using this software, the anatomical structure of interest (e.g. head) is first segmented (isolated) from the 3-D data set. Then, the volume of interest is saved and a special data format such as STL (data transmission format) is generated. The data file is then transferred to a rapid prototype apparatus in a readable format. The above-mentioned off-set is an estimated value to facilitate the use of the printed masks, for example making it easier for the patient to pull the mask on and of i.e. to remove the masks without scratching the skin and to allow for a comfortable wear thereof. A positive off-set can be created to increase the level of comfort or to give room for hair or other objects. A negative off-set is used to improve the level of tightness. Another reason for the off-set is to compensate for dimensional variations during the obtaining of the surface data. Marks, such as cross hairs and cutting edges, can be directly inserted into the model. Non-existing data may be added to close gaps or passages of non-existing data. Optionally, foramina for mouth, nose and ears are included in the data sets and a positive or negative off-set may be created in this respect. Furthermore, it is possible to create zones of reduced or increased thickness of the material to influence radiation behavior.

Also foramina for e.g. nose, mouth, ears and other outjutting body parts as well as for foramina required for radiation treatment reasons can be excised. Still further, mounting devices for adjusting the complete mask, e.g. to the radiation couch can be inserted into the material as well. Finally, the surface model is printed out using an appropriate 3-D rapid prototyping print technique.

The device allows for an exact verifiable and reproducible positioning of a body part with respect to the radiation beams. In radiation therapy, tumorous tissue of the human body is treated with high-energy radiation. The application thereof has to be exactly controlled in order to deliver a dose to the entire tumor and to minimize damage to the neighboring healthy tissue. Since most of the radiation therapy is performed by an external source radiation therapy device, such as a linear accelerator which produces high energy X-rays, healthy tissue is almost every time affected by the radiation beam. The mask may be equipped with a fixation device connected to the treatment couch or place reducing movement of the human body to a minimum or even eliminating it. Therefore, the fixation device according to the present invention helps minimizing radiation to healthy tissue while maximizing the amount of delivered dose to the tumor. This optimizes the application of the predetermined dosage delivered to the tumorous tissue and to keep the healthy tissue out of the range of the high energy X-rays.

The manufacturing of the mask or fixation device (to fix the mask to e.g. a table) can be carried out by all the today available rapid prototyping technologies, e.g. by a layer-by-layer-based process such as 3-D printing, stereolithography (SL), selective lasers sintering (SLS), direct mass sintering (DMS), fused deposition modeling (FDM), poly-jet modeling (PJM) or others.

Preferably, the fixation device, particularly a mask for medical purposes such as radiation therapy, is formed by 3-dimensional (3-D) printing devices in which the fixation device is printed as a positive layer by layer which 3-D printers comprise a product-cavity allowing for manufacturing layer by layer a fixation device such as a mask or other devices for medical purposes in a size 600×500×400 mm$^3$. Therefore, the fixation device can be built in a 1:1 scale.

Larger parts, such as extremities of the human body, e.g. legs or arms, could be manufactured by the 3-D rapid prototyping apparatuses such as 3-D printers in smaller segments which are finally completed and comprise a plurality of segments, to give an example. Alternatively, such larger parts of a prosthesis or parts of a prosthesis, complete legs or arms of the human body are manufactured in prototyping machines, 3-D printers to give an example, in a larger size and scale. The prototyping devices are facing a rapid development into larger scales and sizes and higher performance, i.e. higher production speed.

On the other hand, the fixation device, particularly a mask for medical purposes such as radiation therapy could be manufactured as a negative impression of the surface which serves the purpose to manufacture the fixation device, a mask or the like, by casting the part out of a special material with biocompatible properties or to manufacture the fixation device or mask with a material which has special properties concerning radiation absorption. Furthermore, inserts and inlays can be cast into the mask to act as fixation, hinges or reference points, reinforcing reasons or radiation fielding reasons and the like.

In both cases, imaging data is obtained from CT, MRI or optical 3-D scanners. The imaging data is being prepared and converted into stl or vmrl-format, non-existing data which may exist is added to close the loops or passages. Optionally, foramina for mouth, nose and ears are included in the datasets, an off-set is created to increase comfort for the patient and in preparation of the 3-D data certain points for fixations or calibrations are being applied. Still further, it exists the possibility to create zones of reinforcements in the material to influence radiation.

According to the first aspect of the present invention which has been described before in great detail, the imaging data which is used to create a fixation device such as a mask for medical purposes, i.e. radiation therapy treatment purposes is based on high spatial resolution imaging data. This high spatial resolution imaging data allows for exact and reproducible re-positioning of the mask minimizing motion artefacts. For each treatment session, a more reproducible position during long-term follow-up can easily be found. Initial and follow-up imaging, therefore, strongly depend on correct and reproducible positioning of the patient. Placing a patient in a mask produced by rapid prototyping meets these requirements minimizing also motion artefacts during the treatment which in turn increases data quality.

According to this first aspect of the present invention relating to treatment planning for instance radiation therapy, treatment planning, the masks may be manufactured by 3-D printing, layer-by-layer to give an example. By means of this technique, a creation of the wall thickness of the generated mask, to give an example, can easily be performed, maintaining a positive or negative off-set, depending on the requirements. A variation in thickness of the fixation device, such as an individual mask, decreases or increases—if necessary—the dosage of radiation beams applied to affected tissue. By means of the variation of the thickness of the individual fixation device or the individual mask very sensitive areas, such as the eyes, may be protected against the radiation beams. The radiation beams can be directed depending on the variation of thickness of the mask directly to the areas of the affected tissue. By the variation of thickness of the fixation device such as the mask healthy tissue is protected from the radiation beams, and radiation therapy consequently is focused on those areas of tissue which are affected. This protective effect depends on the variation of thickness which can be individually modeled, based on the non-invasive imaging data obtained. Still further, variation of thickness allows for forming inserts within the wall into which protecting elements made from lead or from copper can be inserted which absorb radiation beams. The inserts may be made from lead or copper to protect sensitive areas, for example the eyes, to be exposed to radiation beams which may damage intact human structures. Alternatively to lead and copper, to give examples for metals, bisphosphates are suitable for absorbing radiation beams during radiation therapy of tissue affected.

According to a second aspect of the present invention, in addition to "conventional 3-D imaging", image acquisition of a volume over time (functional imaging) allows to visualize and to describe patho-physiological features of the tumor. This 4-D technique allows for calculation of functional maps of pathological properties within the tumor that may offer an additional target strategy for treatment planning, e.g. radiation boosts or radiofrequency application. According to the 4-D technique, an orienting of radiation planning in view of affected tissue and healthy tissue is not only based on anatomical structures, but likewise is based on imaging data when correlated with time to show interactions between the tumor and its surroundings within the human body.

Accordingly, a third aspect of the present invention, a "mirror technique" is disclosed. By means of mirror technique, anatomical structures of the human body can be built—if not existing such as prostheses—or rebuilt if lost, e.g. during injuries or during an accident by mirroring existing anatomical structures to the opposite side using voxel replacement technique. Based on individual human body structures, imaging data of which is obtained by the above-described imaging techniques CT, MRI, PET or the like being available and based on individual human body structures still intact the structures can be mirrored and/or rebuilt to fill in the missing structures. With this technique, a prosthesis or epithesis of anatomical structure which got lost such as an extremity or just a piece of bone, destroyed or never created can be rebuilt or newly built, respectively. This offers a new approach and a new area of use for the manufacturing of prostheses or of epitheses as disclosed in GEHL, G., SAILER, H. F., ZOLLIKOFER, C. E., STUCKI, P.: Epithetic Treatment Principles and Use of Stereolithography, Journal of Cranio-Maxillofacial Surgery, Vol. 24, Supplement 1, 1996, 46).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1.1 is a virtual 3-D image of the region of interest, i.e. a ventricle;

FIG. 5.1 shows a still intact healthy structure of the human body such as the left hand; and FIG. 5.2 shows a reconstructed right hand of a patient which has been reconstructed according to the shape of the still intact left hand of the patient given in FIG. 5.1.

DETAILED DESCRIPTION

Figure 1:
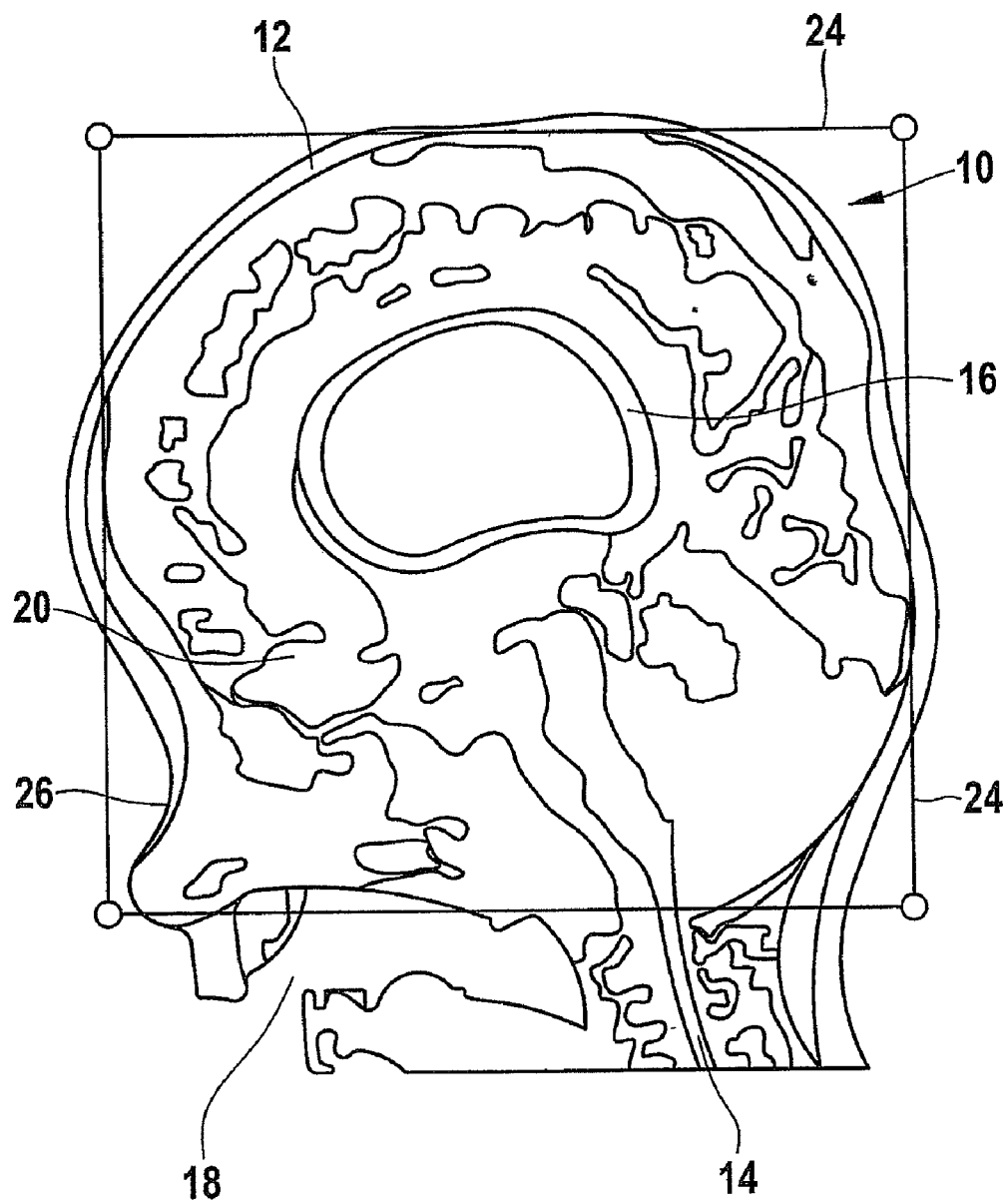
FIG. 1 shows a 2-D image of a part of the human body, e.g. the head.

According to FIG. 1, a body-part of the human body, for instance the head of a child, is shown as an image taken by non-invasive imaging technology. In this context, non-invasive imaging technologies are computer tomography or magnetic resonance imaging or position emission tomography or surface scans and others. Non-invasive imaging technologies further include optical imaging, ultrasound or laser 3-D scanning and other techniques. More specifically, optical imaging includes a stroboscopic measurement method using a stroboscope or a timing light or, in the alternative, a rotary rotating or revolving shutter to create a stroboscopic effect.

In the image given in FIG. 1 a child's skull 12 is shown. Reference no. 14 labels the spine, reference no. 16 a ventricular cavity within the skull 12. Reference no. 18 depicts the mouth; one of the child's eyes is labeled with reference no. 20. A detecting area is identified by reference no. 24 and has a substantially square shaped configuration. The substantially square shaped configuration, i.e. setting area 24 represents a single 2-D detecting layer. It is to be understood that upon non-invasive imaging technologies such as computer tomography, magnetic resonance imaging, the body part 10, i.e. the skull 12, is divided in a plurality of layers 26 each stacked above the other. This offers a 2-D image according to the depth of the 2-D layers 26. In a right angle oriented with respect to the detection area 24, i.e. the 2-D detecting layer according to FIG. 1, further detecting areas oriented perpendicular to the drawing plain given in FIG. 1 are imaged. Thus, the body part 10, i.e. the child's skull 12, is being layered in detecting areas oriented perpendicular to the drawing plain given in FIG. 1.

The non-invasive imaging technology such as CT or MRI applied combining the layers in X, Y, Z-direction for a 3-D perspective view of the body part being imaged. This in turn results in a plurality of imaging data which allows for a reconstruction of the outer contour of the body-part 10, i.e. the skull 12 given in FIG. 1, out of the data already stored.

In the image given in FIG. 1, a ventricular cavity 16 is present within the skull 12. Still further, the skull's 12 outer contour is imaged by the wide rim providing information on the surface of the skull in the respective 2-D layer 26 as given within the detecting area 24 according to FIG. 1.

Out of the data of one single layer 26 and by combining the data of one layer 26 with data of the subsequent 2-D detecting layers 26 the virtual image according to FIG. 1.1 is generated.

In the perspective view according to FIG. 1.1, a 3-D picture of inner structures being present within the child's skull 12 according to FIG. 1 are visualized. In FIG. 1.1, the virtual 3-D view of inner structures is shown. Reference no. 14 depicts the spine at the lower region of the inner structure shown in the 3-D picture 22 according to FIG. 1.1.

By combining X, Y, Z oriented data provided by non-invasive imaging technologies such as CT and/or MRI, the data present is used to derive from the data stored and present a 3-D model of outer surfaces such as the surface of a skull or such as the surface given in perspective view in FIG. 1.1, representing a 3-D model.

After the data acquisition is performed, segmentation is conducted to isolate the relevant anatomical structure from the 3-D or 4-D data obtained by non-invasive imaging techniques. If necessary, the isolated data can be rearranged in different scales to show details prior to converting the data into a machine-readable data set for rapid prototyping techniques as mentioned above. After the segmentation of the relevant anatomical structure, a digital surface is created. This digital surface either represents an inner surface from the interior of the human body such as the contour of a ventricle or an outer surface such as the contour of the face of a patient. Both approaches are feasible using the data obtained from non-invasive imaging techniques. This digitally created surface is stored in a readable format for a rapid prototyping device. This is either the inner or outer surface of the structure to be modeled by means of the 3-D printing technique, to give an example. This approach allows the application of the "mirror technique" by means of which parts of the human body, which may be caused upon accidents can be rebuilt by using the data of anatomical structures still intact. This in turn means that, to give an example, a leg can be rebuilt by using the outer surface as a digital surface which forms the basis of a prostheses for a new leg to be remodeled by using the present invention as a rapid prototyping technique for the manufacturing of prostheses and epitheses.

Figure 2:
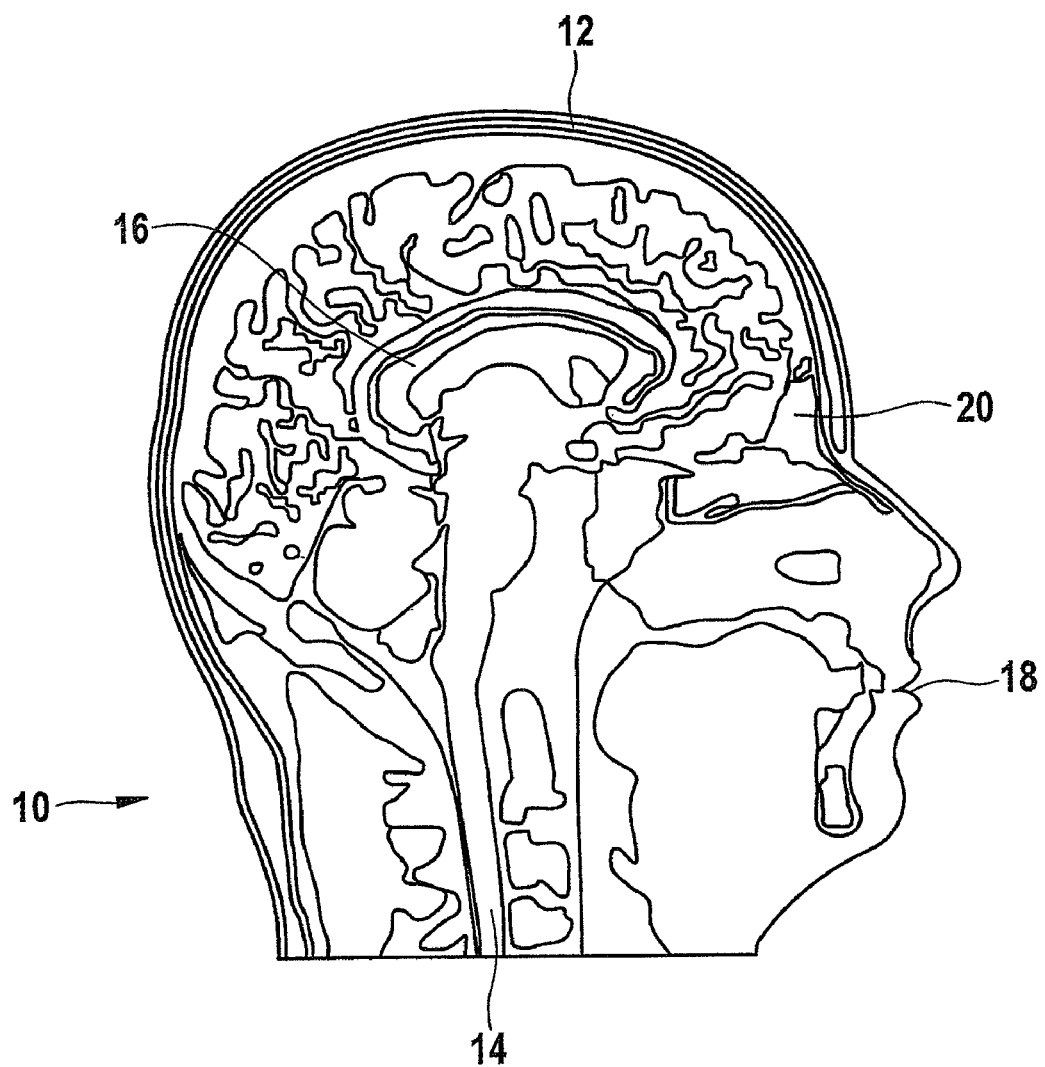
FIG. 2 is a 2-D side view of an image taken by CT, or MRT or PET.

FIG. 2 shows a further image view in the X, Y plane being taken by the non-invasive imaging technology.

According to the 2-D image given in FIG. 2, the body-part 10 given in FIG. 2 represents a skull 12, a human eye 20, a mouth labeled with reference no. 18 and a spine 14 extending from the part of the body given in FIG. 2 into the spiral channel not shown in greater detail according to the view in FIG. 2.

The data given in FIG. 2 constitutes a single 2-D layer being similar to the single 2-D detecting layer 26 being arranged within the detecting area 24 according to FIG. 1. According to the view given in FIG. 2, representing a single 2-D detecting layer 26 in this X, Y plain information on the surface contour, i.e. of the contour of the outer circumference and the outer contour of the skull 12 according to FIG. 2 is present. Still further, in the layer shown in FIG. 2, the ordinates of the nose, the eye 20 and the mouth 18 can be reconstructed. Given the multitude of layers 26 being imaged by means of non-invasive imaging technology an entire human skull 12, i.e. the outer surface of the skull 12 can be reconstructed by means of the present invention by means of data already present by non-invasive technologies such as computer tomography and magnetic resonance imaging.

Perpendicular to the drawing plain according to the 2-D detecting layer 26 according to FIG. 2, a similar plurality of layers oriented in the z direction perpendicular to the drawing plain according to FIG. 2 are available for a reconstruction in three dimensions of the human skull 12 given in FIGS. 1 and 2, respectively in a single 2-D detecting layer 26 only.

Figure 3:
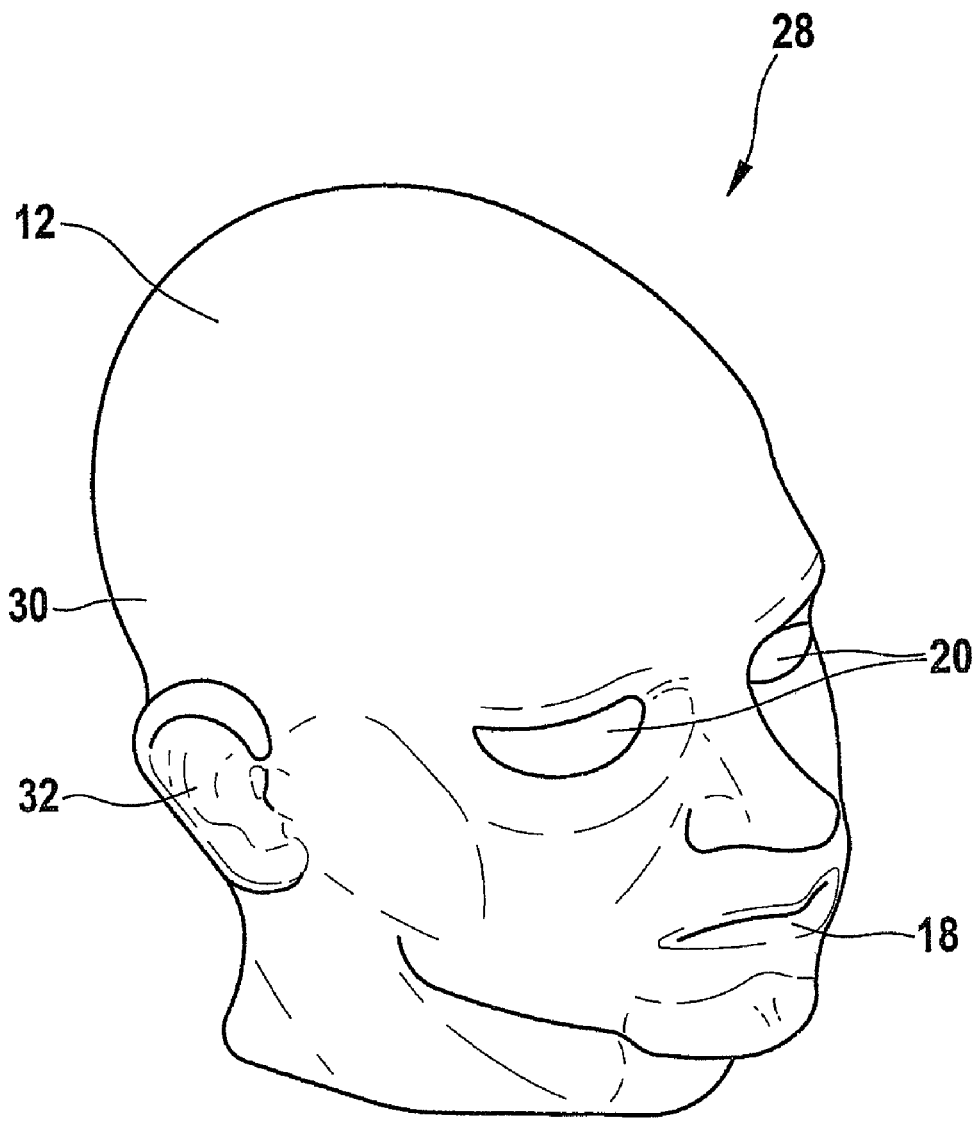
FIG. 3 is a perspective view of a reconstructed head-skull surface, reconstructed from data obtained from non-invasive image technologies.

At hand of imaging data with respect to the outer surface of the skull 12—an example of which is given in FIG. 3—a perspective view is reconstructed. According to the reconstruction given in FIG. 3 in a perspective view, an outer surface 28 of the skull 12 is established with eyes 20, the nose and the mouth 18 in correct positions. Still further, both ears 32 are represented. The perspective 3-D image given in FIG. 3 shows a surface of the head of a human being being reconstructed at hand of imaging data which was initially stored and used to determine a localization of tumors inside the skull 12. On treating the patients by radiation therapy—to give an example—data is obtained which allows for reconstruction of the outer surface of the body-part 10 of a human being which as subject to the non-invasive imaging operation previously performed.

At hand of the data initially acquired with respect to X, Y 2-D in the X, Y plain 2-D detecting layers and with respect to in that direction oriented detecting layers an entire 3-D reconstruction of the face, i.e. an outer surface of an anatomical structure as shown in FIG. 3, the entire skull 12 given all its contours is feasible by using the present invention. Alternatively, a ventricle, i.e. an inner surface as shown in FIG. 1 labeled with reference no. 16, can be remodeled as well. These data are processed, segmentation is performed and digital surfaces are generated. The data representing the inner or outer surfaces, respectively, is converted to machine-readable processing data at hand of which the inner or outer surface, i.e. the contour of a human face, is created.

Figure 4:
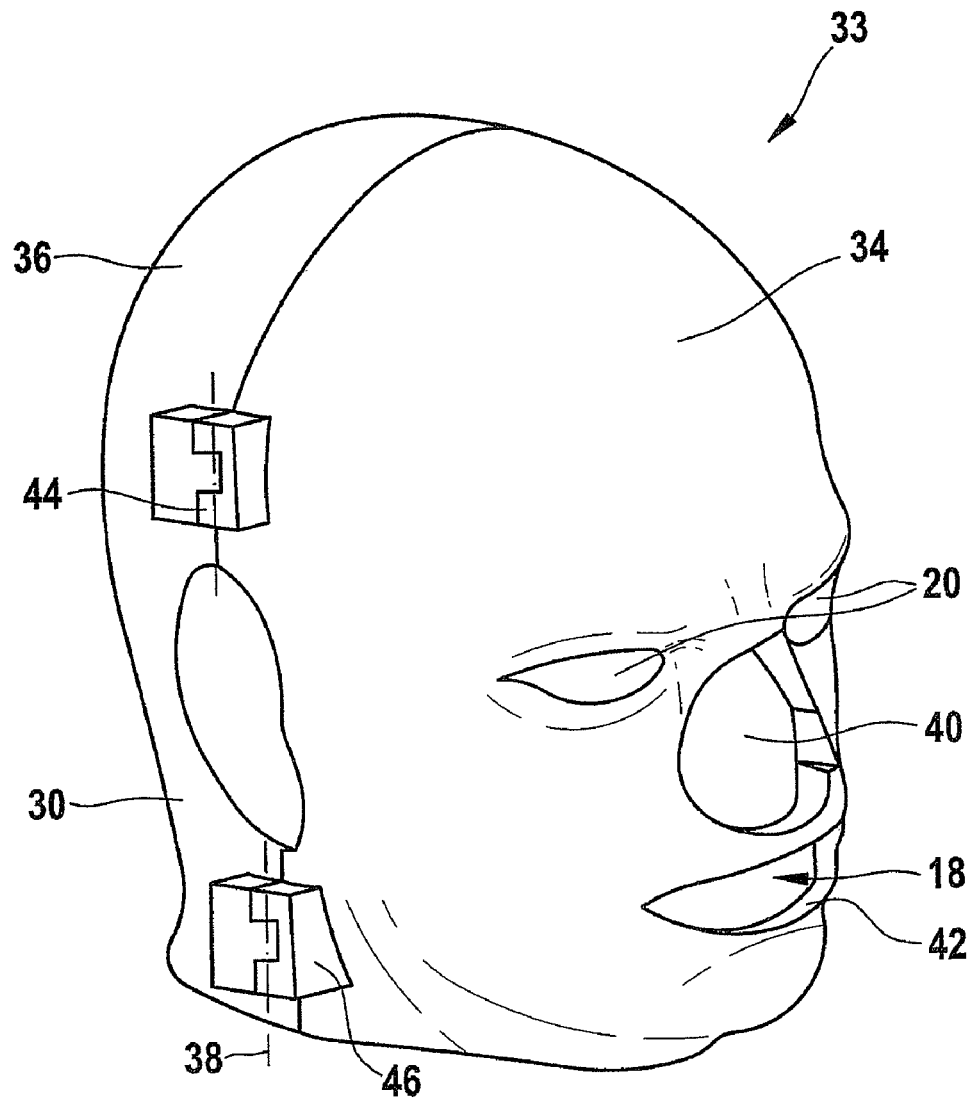
FIG. 4 is a perspective view of a fixation device such as a mask.

FIG. 4 shows an example of a fixation device for applications in radiation therapy, particularly the mask. It is understood that alternatively to the fixation device, particularly shaped as a mask, other medical instruments such as a prosthesis for a part of the human body could be manufactured analogously without departing from the scope of the present invention which is described by example of a fixation device such as a mask.

According to FIG. 4, a fixation device 33 comprises a first half 34 and a second half 36. The first half 34 and the second half 36 according to FIG. 4 are journaled to each other using an upper journal 44 and a lower journal 46. Through both journals 44, 46, a pivot axis 38 extends substantially in vertical direction. The fixation device 33 shown in perspective view according to FIG. 4 is reconstructed based on the reconstructed surface data in the X, Y, Z direction of data sets being obtained in non-invasive imaging technology.

In FIG. 4, it is shown that the first half 34 of the fixation device comprises an opening 40 for the nose shown in FIG. 3 as well as further opening 42 for the mouth 18 likewise shown in the perspective view in FIG. 3.

Thus, no later excision of foramina is necessary anymore which is used presently for the manufacturing of excisions in a fixation device according to the state of the art. The preparation of excisions in the human body has been felt as a very disadvantageous aspect of plaster casting as used as state of the art. In FIG. 4, the first half 34 of the fixation device and the second half 36 of the fixation device are linked with each other by the upper and lower journals 44, 46 respectively, within the rapid prototyping apparatus.

Preferably, the fixation device 33 according to the present invention particularly shaped as a mask is manufactured by use of the 3-D printing process which constitutes a process for quick and efficient manufacturing of 3-D models using 3-D CAD-data without the necessity to use tools or forming devices. The main advantage of the 3-D printing process vis-à-vis other processes is the extremely high manufacturing velocity, low operating costs, simple operation and the use of the reliable ink-jet printing process. 3-D printing constitutes a process to create the fixation device or mask 33 as outlined above as a multi-color model or a single-color model using finite element methods or to create different colors to label different fragments on the fixation device.

Concerning the 3-D printing process, a model such as the fixation device, particularly the mask 33 according to the present invention, is manufactured layer by layer by printing of a liquid binder on a powder material. Typically, a 3-D CAD-data set in stl or vrml-format is created which is prepared for the printing process, particularly is reoriented, positioned and parameterized and is at hand of the 3-D printing software reoriented into a layer model of the fixation device or mask or other medical instrument.

The 3-D printer comprises a cavity within which one or more models, prostheses, fixation devices, parts thereof or masks can be manufactured adjacent to one another or above one another within one operation step.

At the beginning of the printing process, the 3-D printer has been equipped with powder material and liquid binder to ensure that a sufficient amount of material for the following production run is available. As soon as 3-D CAD-data is transmitted and the printing operation has been started, the 3-D printer operates itself without being supervised by operating personnel. The 3-D CAD-data provides for a layer information of each layer of one or more model fixation devices or masks which are to be manufactured within on production run one above the other or one adjacent to the other. By means of 3-D printing a positive or a negative of the device to be manufactured such as a fixation device or a mask 33 or a prosthesis for medical purposes is created. In a first powder layer a first layer of the model to be 3-dimensionally printed is created. After the first layer has been applied, a platform is lowered about the thickness of one layer—typical layer thickness lays in about the range of 0.1 mm—and a new layer of pulverized material is applied. In the next run, the subsequent layer is printed upon the previous layer. This cycle is repeated and the model to be manufactured is being established layer by layer from the bottom to the top.

A typical operation range for one model is dependent on the height thereof and the follow-up thereof about the layers to be created. An average production speed of a 3-D printer is about 25 mm height/h. Upon the ending of the printing process, the models created such as fixation devices or masks 33 or the like or being removed from the surrounding at a pulverized material, serving upon the printing process as reinforcing geometry. This is typically achieved by means of a special device comprising a suction device to remove pulverized material.

After removal of the powder material, the models, fixation device or mask 33 or the like are being transferred to a cabin and are cleaned. The powder material surrounding the model is removed or sucked in as it is being reused within the next process cycle resulting in the consumption of material being equal to the volume of the model being created. A reinforcing structure is maybe not necessary and might be used optionally.

Depending on the pulverized material and the application purpose, the models created in 3-printing based upon 3-D CAD-data in stl or vrml-format are being infiltrated for instance by a liquid medium such as wax, varnish or resin to increase the mechanical properties of the model, i.e. the mask 33. The depowdered mask 33 may be infiltrated with one component resin or with two or more component setting resins. The infiltrant may be applied by dipping, spraying, pouring or by using a brush. Vacuum can be applied to increase the infiltration depth. Depending on the used resin or infiltrant, the mask 33 stabilizes and dries up at room temperature. The drying time can be shortened by applying a higher temperature level. During or after the infiltration, reinforcing layers of glass fiber, carbon fiber, textile fibers or other reinforcing material can optionally be applied to either side of the mask 33 or fixation device 33, respectively. Additional fixtures for aligning the parts, reference points to the patient bench, hinges, locking devices and the like are fixed to the mask if not already inserted upon manufacturing of the mask 33 via 3-D layer-by-layer printing, to give an example. After an infiltration of the 3-D printed product they could be further processed. Varnish could be applied if appropriate. Still further, a smoothing of the surface is feasible by grinding or sanding as appropriate and depending on the expected surface roughness. Then, they are ready for use.

The fixation device 33 comprising the first half 34 and the second half 36, respectively, can be manufactured within the rapid prototyping (RPT) device or be added after production as described above.

On the surface of the first half 34 or the second half 36 of the fixation device 33 given in perspective view in FIG. 4 markers or crosshairs or the like, are conceivable constituting target points for the medical personnel doing radiation therapy to direct the high-energized X-rays on tumorous tissue to be treated by X-ray therapy. As a consequence, healthy tissue within the skull 12 to which no markers are assigned is not harmed by the high-energized X-rays upon radiation therapy.

Still further, upon rapid prototype manufacturing of the fixation device 33 as shown in FIG. 4 inserts can be placed within the surface which allow for a precise positioning of the patient wearing the mask or the fixation device 33, respectively, on a radiation couch upon establishing radiation therapy.

The 3-D printing process for the creation of the fixation device 33, or the mask, respectively is simplified to operate and increases safety of the manufacturing process. Alternatively, to the 3-D printing layer-based process rapid prototyping technologies are available today. Besides a layer-by-layer based process such as 3-D printing, stereolithograhpy (SL), selective laser sintering (SLS), direct mass sintering (DMS), fused deposition modeling (FDM) or poly-jet modeling (PJM) may be techniques suitable for the production of the fixation devices 33 or masks 33, respectively. In view of the high speed of the 3-D printer in the formation of 25 mm of height/h a model such as a fixation device or mask 33 according to the present invention is to be manufactured within a couple of hours. Still further, the 3-D printing technique comes along with low printing, low operating costs and a support structure is not necessarily required. The technique applies a high productivity and uses material without any risks. Still further, color segments can be created upon manufacturing of the models, i.e. for radiation therapies special fixation inserts could be integrated into the structure to be created during the manufacturing process by means of the 3-D printer. The size of the model to be created by the 3-D printing technique is about 600×500×400 mm$^3$, which is a fast growing technique so that larger scales or sizes of such prototyping devices are available within the near future. This, in turn, allows for the rebuilding or remodeling of larger parts of the human body, such as legs or arms, in one operation without the requirement of remodeling a larger part of the human body out of a number of different components to form one part.

Within the 3-D printing technology, a negative could be manufactured as well which is subsequently applied with a liquid having plastic properties or having properties which influence radiation therapy according to application purposes. The material to be inserted into the negative cavity of the model can be chosen such that radiation properties, radiation absorption phenomena could be influenced. Still further, foramina reinforcements, openings for mouth, nose and ears could be excised upon preparation of the 3-D CAD-data obtained from the data present by non-invasive imaging technologies such as CT and MRI, as outlined above.

According to a further aspect of the remodeling of the fixation device 33 or the mask 33, respectively, a variation of thickness of the respective fixation device can be obtained easily upon manufacturing thereof via a rapid prototyping apparatus such as a 3-D printing device. According to the imaging data obtained by non-invasive imaging technology as outlined above, a variation in thickness of the fixation device 33 or the mask 33 allows for a protection of sensitive areas such as eyes from radiation beams which may affect those. A variation in thickness of the wall of the fixation device 33 or the mask 33 allows for a variation of absorption properties for radiation beams. By means of a variation of thickness and taking into account a positive or negative to the surface of the human body, i.e. the outer contour of the face, a variation of the degree of protection can easily be obtained during manufacturing of the fixation device 33 or the mask 33, respectively. This in turn allows for focusing the radiation beams on tissue affected and in turn to protect healthy tissue from being damaged by radiation beams. These two aspects in turn allow for an increased efficiency of radiation therapy treatment planning.

According to a further aspect of the present invention which has been described herein in terms of an individually generated fixation device or a mask 33, respectively, the present invention could be used in addition to 3-D imaging technologies while image acquisition of a volume is correlated with time. This means 4-D technique, functional imaging is applied. Functional imaging allows to visualize and to describe path-physiological features of the tumor. This 4-D technique allows calculating functional maps of pathological properties within the tumor that may offer an additional targeting strategy for treatment planning (e.g. boost radiation, radio-frequency application, or to orient radiation planning not only based on anatomical structures but rather considering a development occurring over a certain period of time. If 4-D technique is applied with respect to an affected tissue the growth or changes in shapes can be made visible and the tumor development or a tumor growth can be shown in an accelerated film which allows the medical personnel to estimate consequences for the health of the patient. This further aspect of the present invention allows for a therapy monitoring, i.e. an estimation for the medical personnel whether the radiation dose applied to affected tissue is efficient, i.e. whether or not the size of tumorous tissue decreases or increases when seen over the time period of the radiation therapy.

Still another aspect according to the present invention is the application of the "mirroring"-technique. FIG. 5.1 shows a still intact human structure such as a hand 50 with a number of fingers 52 and a thumb 54. This human structure, i.e. the hand 50 as shown in FIG. 5.1, can be treated by a non-invasive imaging technique to obtain data to remodel the intact human structure 50 as shown in FIG. 5.2. According to this third aspect of the present invention, the intact human structure 50 is mirrored, i.e. the affected or non-present hand 56 shown in FIG. 5.2 is remodeled, i.e. rebuilt, by a rapid prototyping technique, i.e. 3-D printing, such as 3-D layer-based printing. In this respect, the present invention offers the possibility to build or rebuild an anatomical structure 56 by mirroring an existing anatomical structure 50 to the opposite. This means a leg or an arm or another part of the body which has been severely injured upon the occurrence of an accident or the like is to be remodeled using the present invention. The remodeling is performed by mirroring a still intact anatomical structure such as a leg or an arm or part of an arm—just to give an example—by using voxel replacement technique. The voxel replacement technique is based upon the data obtained from non-invasive imaging technologies such as CT or MRI to give examples to obtain a digital surface in which missing parts or missing data is reconstructed to arrive at smooth surface structures of an anatomical surface. Based on individual human body structures that are available and which are still intact these parts of the human body can be mirrored and/or rebuilt to fill in the missing structure. With this technique a prosthesis or epithesis of anatomical structures which got lost, for example the above-mentioned extremity, or just a piece of bone or the like, or which have been destroyed for one reason or the other or never were created can be rebuilt or newly built, respectively. Again, data acquired by non-invasive imaging techniques are post-processed into a model by means of imaging post-processing software. Using this software the anatomical structure of interest is pigmented or isolated from a 3-D data set. This data is then transferred to a rapid prototype apparatus in a readable format. This rapid prototype apparatus can be chosen out of techniques such as layer-based 3-D printing or stereolithography (SL), selective laser sintering (SLS), direct mass sintering (DMS), fused deposition modeling (FDM), poly-jet modeling (PJM) or other techniques.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method to derive an artificial anatomical structure from imaging data of an anatomical structure obtained by a non-invasive imaging technology, the non-invasive imaging technology including computed tomography (CT), magnetic resonance imaging (MRI), optical imaging, ultrasound or laser 3-D scanning, the method comprising:
    a) obtaining the imaging data of the anatomical structure via the non-invasive imaging technology;
    b) performing digital segmentation, isolation, or both of the imaging data of the anatomical structure;
    c) performing data transformation for 3-D reconstruction of an inner surface or an outer surface of the anatomical structure or performing reconstruction of the anatomical structure by mirroring data of the anatomical structure; and
    d) generating the artificial anatomical structure by a rapid prototyping technique, and upon rapid prototyping the artificial anatomical structure, hollow cavities are created into which a radiation influencing material including lead, copper, or bisphosphates are inserted to influence radiation beam distribution upon radio therapy treatment,
    wherein according to method step c) the artificial anatomical structure is generated in at least two parts for radiation therapy treatment, and
    wherein the artificial anatomical structure is generated with a variation in wall thickness to protect healthy or sensitive tissue from radiation beams and to focus radiation beams on affected tissue.

2. The method according to claim 1, wherein by adding or subtracting data a complementation of data for 3-D remodeling is performed.

3. The method according to claim 1, wherein the artificial anatomical structure comprises a partial or complete off-set, wherein the partial or complete off-set is a positive or a negative off-set.

4. The method according to claim 1, wherein the artificial anatomical structure comprises foramina for ears, nose and eyes and other parts of the human body.

5. The method according to claim 1, wherein a digital complementation of data into a fixation geometry is performed to allow fixation of separate parts of the artificial anatomical structure to a treatment area.

6. The method according to claim 1, wherein upon generating the artificial anatomical structure, a manual complementation of a fixation geometry is performed during or after a printing process to improve positioning of the artificial anatomical structure in a treatment position.

7. The method according to claim 1, wherein according to step d) the artificial anatomical structure is generated by the rapid prototyping technique based on a layer-by-layer technique.

8. The method according to claim 1, wherein according to step d) the artificial anatomical structure is generated by use of the rapid prototyping technique based on a 3-D printing technique.

9. The method according to claim 1, wherein the artificial anatomical structure obtained according to step d) is treated by powder, glue or a binding material to improve mechanical stability thereof.

10. The method according to claim 1, wherein according to step d) the artificial anatomical structure is generated by the rapid prototyping technique based on plaster.

11. The method according to claim 1, wherein according to step d) the artificial anatomical structure is generated by the rapid prototyping technique based on starch.

12. The method according to claim 1, wherein the artificial anatomical structure is applied with a soft material to improve a patient's comfort.

13. The method according to claim 1, wherein according to step d) markers are introduced upon generating the artificial anatomical structure allowing for positioning and repositioning of the artificial anatomical structure.

14. The method according to claim 1, wherein the material of the artificial anatomical structure is infiltrated after initial production with an after-treatment liquid.

15. The method according to claim 1, wherein the artificial anatomical structure is produced based on a negative form.

16. The method according to claim 1, wherein according to method step c) the artificial anatomical structure is reconstructed by mirroring 3-D imaging data of an outer or inner surface of the anatomical structure.

17. The method according to claim 1, wherein after method step d) a grinding or sanding of the artificial anatomical structure is performed.

18. A method, comprising:
    post-processing imaging data acquired by a non-invasive imaging technology into a surface model;
    generating a fixation device by a rapid prototyping technique based on the surface model,
    wherein zones of reduced or increased wall thickness of a material making up said fixation device are created to influence a radiation beam distribution upon radio therapy treatment, wherein said fixation device is generated with a variation in wall thickness to protect healthy or sensitive tissue from radiation beams and to focus radiation beams on affected tissue.

19. The method according to claim 18, wherein the variation in wall thickness forms inserts or cavities into which protecting elements made from lead, copper, or bisphosphates are inserted.

20. The method according to claim 19, wherein said inserts or cavities with the protecting elements protect sensitive areas from being exposed to radiation beams, which may damage intact human structures.

21. The method according to claim 18, wherein the fixation device comprises a mask and mounting devices for adjusting the mask, wherein the mounting devices are integrated into a material of the mask.

22. The method according to claim 18, wherein upon generating the fixation device, a manual complementation of a fixation geometry is performed during or after a printing process to improve positioning of the fixation device in a treatment position.

23. The method according to claim 18, wherein imaging data is correlated with time to allow for functional therapy monitoring over therapy time for visualization of a body portion showing patho-physiological features of a tumor, and
wherein function maps of pathological properties are calculated offering a specific target strategy for treatment planning, including radiation boosts or radio frequency applications.

24. A fixation device for radiation therapy of a patient, wherein the fixation device is generated by means of 3-D rapid prototyping by using imaging data obtained from a non-invasive imaging technology,
wherein the fixation device includes zones of reduced or increased wall thickness to influence radiation behavior, and
wherein the variation in wall thickness protects healthy or sensitive tissue from radiation beams and focuses radiation beams on affected tissue.

25. Artificial anatomical structures, pathological structures, or both, wherein the anatomical structures, pathological structures, or both are generated by means of 3-D rapid prototyping by using imaging data obtained from non-invasive imaging technologies.

26. A fixation device, comprising:
a body portion having a shape corresponding to an outer surface of a human body portion, the body portion including a first half and a second half;
a connection device coupling together the first half and the second half of the body portion;
inserts disposed within the body portion, the inserts configured to position a patient wearing the fixation device onto a surface; and
radiation influencing material disposed within the body portion, the material comprising lead, copper, or bisphosphates,
wherein the body portion includes zones of reduced or increased wall thickness.

27. The fixation device according to claim 26, further comprising markers disposed on an outer surface of the body portion.

* * * * *